US006482824B1

(12) United States Patent
Clark et al.

(10) Patent No.: US 6,482,824 B1
(45) Date of Patent: Nov. 19, 2002

(54) USE OF N-SUBSTITUTED (3,6-DIHYDRO)-2H-1,2-OXAZINE DERIVATIVES AS SELECTIVE MGLUR1 ANTAGONISTS

(75) Inventors: Barry Peter Clark, Hampshire (GB); John Richard Harris, Surrey (GB); Ann Elizabeth Kingston, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/830,873

(22) PCT Filed: Nov. 1, 2000

(86) PCT No.: PCT/GB99/03607

§ 371 (c)(1),
(2), (4) Date: Jul. 30, 2001

(87) PCT Pub. No.: WO00/26199

PCT Pub. Date: May 11, 2000

(30) Foreign Application Priority Data

Nov. 2, 1998 (GB) ............................................. 9823845

(51) Int. Cl.$^7$ ..................... A61K 31/535; C07D 265/02
(52) U.S. Cl. .............................. 514/228.8; 514/230.5; 544/63
(58) Field of Search ......................... 544/63; 514/228.8, 514/230.5

(56) References Cited

FOREIGN PATENT DOCUMENTS

| GB | 1 221 734 A | 2/1971 |
|---|---|---|
| WO | WO 96 05828 A | 2/1996 |
| WO | WO 99 26927 A | 6/1999 |
| WO | WO 99 54280 A | 10/1999 |

OTHER PUBLICATIONS

Labaziewicz H. et al.: The synthesis and spectral properties of N–(3,4,5–trimethoxybenzoyl)–3,6–dihydro–1, 2–oxazines and N–(3,4,5–trimethoxybenzoyl)tetrahydro–1, 2–oxazines: HETEROCYCLES, NL., ELSEVIER SCIENCE PUBLISHERS B.V., AMSTERDAM, vol. 34, No. 4, Apr. 1992, pp. 699–711, XP002131089 formulae (4) and (5), p. 701.

Primary Examiner—Richard Raymond
(74) Attorney, Agent, or Firm—Alexander Wilson

(57) ABSTRACT

Use of a compound of formula (I) in which, $R^1$, $R^2$ and $R^3$ are independently hydrogen, $(C_1-C_6)$alkyl, $(C_2-C_6)$alkenyl, $C_3-C_{10}$)cycloalkyl, unsubstituted or substituted aryl, unsubstituted or substituted aryl$(C_1-C_6)$alkyl, unsubstituted or substituted aryl$(C_2-C_6)$alkenyl, halo, carboxy, $(C_1-C_6)$ alkoxycarbonyl or —$(CH_2)_m$—OH wherein m is 1, 2 or 3; - - - indicates a single or a double bond; X and each independently hydrogen, or X and Y together represent a bridge of the formula —$(CH_2)_m$—, where n is 1 or 2; $A_1$ and $A_2$ are each independently an unsubstituted or substituted aryl; Z is —CO—, —$SO_2$— or —$CH_2$; provided that, when Z is —CO—, $A_1$ is not 3,4,5-trimethoxyphenyl; or a pharmaceutically-acceptable salt or ester thereof, for the manufacture of a medicament for the treatment of a condition indicating the administration of a selective mGluR1 antagonist.

9 Claims, No Drawings

USE OF N-SUBSTITUTED (3,6-DIHYDRO)-2H-1,2-OXAZINE DERIVATIVES AS SELECTIVE MGLUR1 ANTAGONISTS

This application is a 371 of PCT/GB99/03607, filed Nov. 1,2000

This invention relates to novel chemical compounds and their use as pharmaceuticals.

It is known that excitatory neurotransmission in the mammalian central nervous system is primarily mediated by the amino acid, L-glutamate, acting on ionotropic and metabotropic receptors, and compounds that modify neurotransmission by interaction with these receptors are of interest for their potential use in the treatment of disorders of the central nervous system.

This invention relates to use of a compound of formula I

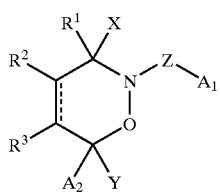

in which,
R$^1$, R$^2$ and R$^3$ are independently hydrogen, (C$_1$–C$_6$)alkyl, (C$_2$–C$_6$)alkenyl, (C$_3$–C$_{10}$)cycloalkyl, unsubstituted or substituted aryl, unsubstituted or substituted aryl (C$_1$–C$_6$)alkyl, unsubstituted or substituted aryl(C$_2$–C$_6$) alkenyl, halo, carboxy, (C$_1$–C$_6$)alkoxycarbonyl or —(CH$_2$)$_m$—OH, wherein m is 1, 2 or 3;
- - - indicates a single or a double bond;
X and Y are each independently hydrogen, or X and Y together represent a bridge of the formula —(CH$_2$)$_n$—, where n is 1 or 2;
A$_1$ and A$_2$ are each independently an unsubstituted or substituted aryl;
Z is —CO—, —SO$_2$— or —CH$_2$—;
provided that, when Z is —CO—, A$_1$ is not 3,4,5-trimethoxyphenyl;
or a pharmaceutically-acceptable salt or ester thereof, for the manufacture of a medicament for the treatment of a condition indicating the administration of a selective mnGluR1 antagonist.

The present invention also provides a method of treating an animal, including a human, suffering from or susceptible to a condition indicating the administration of a selective mnGluR1 antagonist which comprises administering a compound as defined above or a pharmaceutically acceptable salt or ester thereof. The compounds of the invention have been found to be active in tests indicative of their use in the treatment of diseases of the central nervous system such as neurological diseases, for example, neurodegenerative diseases, and as antipsychotic, anticonvulsant, analgesic and anti-emetic agents.

In the above general formula, a (C$_1$–C$_6$)alkyl group can be straight or branched chain, such as, for example, methyl, ethyl, propyl, isopropyl, butyl and isobutyl, and is preferably methyl or ethyl. A (C$_2$–C$_6$)alkenyl group includes, for example, vinyl, prop-2-enyl, but-3-enyl, pent-4-enyl and. isopropenyl, and an alkenyl group can contain more than one double bond and, in addition, one or more triple bonds. A preferred alkenyl group is of the formula R'—CH=CH— where R' is C$_1$–C$_4$ alkyl.

A (C$_3$–C$_{10}$)cycloalkyl group is preferably, for example, cyclopropyl, cyclobutyl; cyclopentyl or cyclohexyl and these groups may optionally be substituted by one or two C$_1$–C$_4$ alkyl, for example methyl, or ethyl substituents.

An unsubstituted or substituted aryl group includes aromatic and heteroaromatic rings, such as phenyl, napththalene, benzodioxan, thiophene, furan, pyrrole, imidazole, thiadiazole, pyridine, oxazole, benzofuran, indole and thiazole. An unsubstituted or substituted aryl (C$_1$–C$_6$)alkyl group is one such aryl group linked through an alkylene chain, for example, aryl- (CH$_2$)$_n$ where n is 1 to 6, and a most preferred example is benzyl. An unsubstituted or substituted aryl(C$_2$–C$_6$)alkenyl is one such aryl group linked through an alkenylene chain derived from an alkenyl group as defined above, and preferably of the formula arly- (CH$_2$)$_n$ CH=CH— where n is 1 to 4.

In the above general formula, when an aryl group is substituted, it is substituted with, for example, one or ore substituents, preferably 1 to 3 substituents, selected from (C$_1$–C$_6$)alkyl, hydroxy, (C$_1$–C$_6$)alkoxy, (C$_1$–C$_6$)alkylthio, halo, trifluoromethyl, cyano, nitro, amino, (C$_1$–C$_6$) alkylamino, (C$_1$–C$_6$)acylamino, —NHCOO—(C$_1$–C$_6$)alkyl, —NHSO$_2$(C$_1$–C$_6$)alkyl (C$_1$–C$_6$)alkylsulphone or amide.

A halo includes for example fluoro, chloro and bromo, preferably fluoro or chloro.

A (C$_1$–C$_6$)alkoxy or a (C$_1$–C$_6$)alkylthio is an alkyl group linked to an oxygen or a sulphur atom, where the alkyl is as defined above. A (C$_1$–C$_6$)alkoxy or a (C$_1$–C$_6$)alkylthio group includes for example methoxy, ethoxy, methylthio or ethylthio.

A (C$_1$–C$_6$)alkylamino, is an alkyl group linked to a —NH— group, where the alkyl is as defined above. A (C$_1$–C$_6$)alkylamino group includes for example methylamino or ethylamino.

A (C$_1$–C$_6$)acylamino group is an alkyl group linked to an amide group, where the alkyl is as defined above, and is preferably of the formula R—CO—NH— where R is (C$_1$–C$_5$)alkyl.

A (C$_1$–C$_6$)acylamino group includes for example acetamido.

A (C$_1$–C$_6$)alkoxycarbonyl group is an alkoxy group linked to a carbonyl group, where the alkoxy group is as defined above. A (C$_1$–C$_6$)alkoxycarbonyl group includes for example methoxycarbonyl.

A —NHCOO—(C$_1$–C$_6$)alkyl, or a —NHSO$_2$(C$_1$–C$_6$) alkyl group is an alkyl group linked to a group of the formula —NHCOO— or a —NHSO$_2$—, where the alkyl is as defined above. A —NHCOO—(C$_1$–C$_6$)alkyl, or a —NHSO$_2$ (C$_1$–C$_6$)alkyl group includes for example methylcarbamoyl, or methylsulfonylamino.

A (C$_1$–C$_6$)alkylsulphone group is an alkyl group linked to a sulphone group, where the alkyl is as defined above. A (C$_1$–C$_6$)alkylsulphone group includes for example methylsulphone or ethylsulphone. It will be understood that - - - in formula (I) indicates that the bond can be either a single or a double bond. A preferred group of compounds according to formula (I) is one in which - - - indicates a double bond.

It is preferred that R$^1$, R$^2$ and R$^3$ are each independently hydrogen, (C$_1$–C$_6$)alkyl, especially methyl or ethyl, carboxy or —(CH$_2$)$_m$—OH, wherein m is 1, 2 or 3.

It is also preferred that X and Y are each independently hydrogen.

It is especially preferred that A$_1$ is a phenyl substituted 1 to 3 times with a amino, (C$_1$–C$_6$)acylamino, especially acetamido or a —NHCOO—(C$_1$–C$_6$)alkyl, especially methylcarbamoyl. It is also preferred that A$_2$ is a phenyl substituted 1 to 3 times with a (C$_1$–C$_6$)alkoxy, especially ethoxy or ethoxy.

It is further preferred that Z is —SO$_2$— or —CH$_2$—, especially —SO$_2$—.

Especially preferred compounds are of the formula

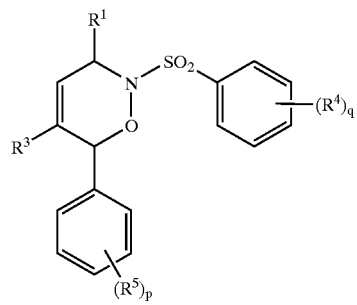

(II)

wherein,

R$^1$ and R$^3$ are each independently hydrogen, or (C$_1$–C$_6$) alkyl, especially methyl;

R$^4$ is amino, (C$_1$–C$_6$)acylamino, especially acetamide, or a —NHCOO—(C$_1$–C$_6$) alkyl, especially methylcarbamoyl;

R$^5$ is (C$_1$–C$_6$)alkoxy, especially methoxy or ethoxy, and p and q are each independently 1 or 2, especially 1;

or a pharmaceutically-acceptable salt or ester thereof.

It will be appreciated that when P is other than one, then the R$^5$ substituents can be different. Similarly. when q is other than one, then the R$^4$ substituents can be different. It is further preferred that the R$^4$ substituent is in the 4 position of the phenyl ring.

Particularly useful compounds of invention are 2-(4-Acetamidobenzenesulphonyl)-3,6-dihydro-3, 5-dimethyl-6-(4-methoxyphenyl)-2H-1,2-oxazine, 2-(4-Acetamidobenzenesulphonyl)-3,6-dihydro-3,5-dimethyl-6-(4-ethoxyphenyl)-2H1,2-oxazine, and 3,6-dihydro-3,5-dimethyl-6-(4-ethoxyphenyl)-2-(4-methylcarbamoylbenzenesulphonyl)-2H-1,2-oxazine, or a pharmaceutically-acceptable salt or ester thereof.

It will also be understood that esters of the compounds of the invention can be prepared and such esters are included in the invention. They can be aliphatic or aromatic such as, for example, alkyl and phenolic esters. The most preferred esters are alkyl esters derived from C$_1$–C$_6$ alkanols, especially methyl and ethyl esters.

It will also be understood that salts of the compounds of the invention can be prepared and such salts are included in the invention. They can be any of the well known acid addition salts. Acid addition salts are preferably the pharmaceutically-acceptable, non-toxic addition salts with suitable acids, such as those with inorganic acids, for example hydrochloric, hydrobromic, nitric, sulphuric or phosphoric acids, or with organic acids, such as organic carboxylic acids, for example glycollic, maleic, fumaric, malic, tartaric, citric, salicyclic or o-acetoxybenzoic acids, or organic sulphonic acids, methane sulphonic, 2-hydroxyethane sulphonic, toluene-p-sulphonic or naphthalene-2-sulphonic acids.

In addition to pharmaceutically-acceptable salts, other salts are included in the invention. They may serve as intermediates in the purification of compounds or in the preparation of other, for example pharmaceutically-acceptable, salts, or are useful for identification, characterisation or purification.

It will be appreciated that the compounds of the invention can contain 1, 2, 3 or 4 asymmetric carbon atoms as indicated by the asterisks in formula (III), and these gives rise to enantiomers. The compounds can be prepared as racemates or as enantiomers, and individual enantiomers can be isolated from racemates by conventional techniques if so desired. Such racemates and individual enantiomers form part of the present invention.

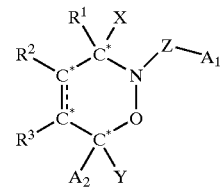

(III)

It is preferred that when - - - is a double bond, the remaining two asymmetric carbons are in a cis disposition regarding R$^1$ and A$_2$, as shown in formulae (IV)a and (IV)b.

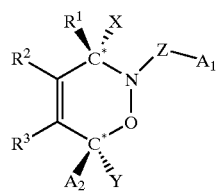

(IV)a

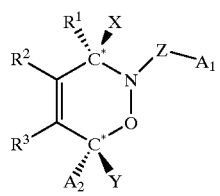

(IV)b

The invention also includes a process for the production of compounds of formula (I), which comprises reacting a compound of formula

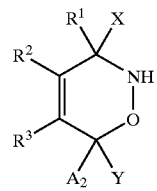

(Ia)

in the presence of a compound A$_1$—Z—L, wherein A$_1$, A$_2$, R$^1$, R$^2$, R$^3$, X, Y and Z have the values defined above, and L is a leaving group, such as for example chloro, bromo or iodo. It is preferred that the intermediate (Ia) is n the form of an acid addition salt. This acid addition salt is preferably addition salt with suitable acids, such as those with inorganic acids, for example hydrochloric, hydrobromic, nitric, sulphuric or phosphoric acids, or with organic acids, such as organic carboxylic acids, for example, maleic, fumaric, malic, or organic sulphonic acids, methane sulphonic, 2-hydroxyethane sulphonic, toluene-p-sulphonic or naphthalene-2-sulphonic acids.

The reaction is carried out preferably at a range of temperatures varying from 0° C. up to reflux. It is also preferred that the reaction is carried out in the presence of a suitable base such as for example triethylamine. It is further preferred that the reaction is carried out in a suitable organic solvent such as dichloromethane. The intermediates A₁—Z—L are readily available or are synthesized by conventional methods. The intermediate (Ia) is prepared via Diels Alder reaction of compounds of formula

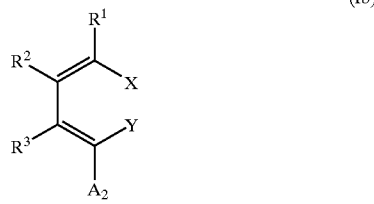
(Ib)

with a compound of formula O=N—Q, wherein A₂, R¹, R², R³, X and Y have the values defined above, and Q is for example —COO'Bu or 1-chlorocyclohexyl.

The Diels Alder reaction is carried out preferably at a range of temperatures varying from 0° C. up to reflux. It is also preferred that the reaction is carried out in a suitable organic solvent such as diethylether, dichloromethane or ethanol. The reagents O=N—Q are readily available. The intermediate (Ib) is prepared by conventional methods, such as for example by dehydrating compounds of formula

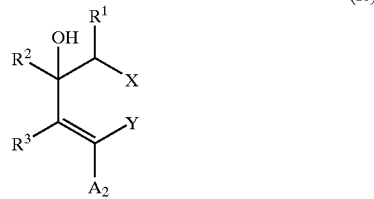
(Ic)

wherein A₂, R¹, R², R³, X and Y have the values defined above.

The dehydration reaction is carried out preferably at a range of temperatures varying from 80° C. up to 150° C., and more preferably under vacuum, such as for example at 4 mbar. It is also preferred that the reaction is-carried out in the presence of a suitable dehydrating agent such as for example potassium hydrogen sulphate. It is further preferred that the reaction is carried out in the presence of a polymerisation inhibitor such as for example hydroquinone.

The intermediate (Ic) is prepared by conventional methods, such as for example reacting-compounds of formula (Id) with organometalic compounds of formula (Ie)

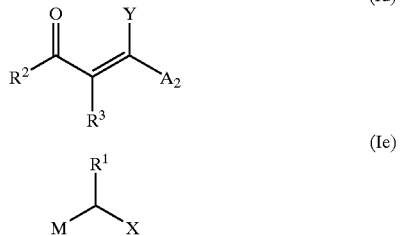
(Id)

(Ie)

wherein A₂, R¹, R²₁ R³, X and Y have the values defined above. The reagent (Ie) is an organometalic compound, such as an organolithium where M is lithium, or a grignard, where M is a(L¹Mg) group, wherein L¹ is a halo, such as for example chloro, bromo or iodo.

This reaction is carried out preferably at a range of temperatures varying from −20° C. up to reflux. It is also preferred that the reaction is carried out in a suitable solvent such as for example diethylether.

The intermediates (Id) and (Ie) are readily available or are synthesized by conventional methods.

An alternative method for the synthesis of intermediate (Ic) is via a Wittig reaction. Compounds of formula (Id) are reacted with compounds of formula (If)

(If)

wherein R¹ and X have the values defined above, and M' is a group of the formula–(PO)—(OR")₂ or —P(R")₃L²', wherein R" is a $C_1$–$C_6$ alkyl and $L^2$ is a halo, such as for example chloro, bromo or iodo.

This reaction is carried out preferably at a range of temperatures varying from −60° C. up to reflux. It is also preferred that the reaction as carried out in a suitable solvent such as for example tetrahydrofuran. It is further preferred that the reaction is carried out in the presence of a suitable base such as for example, n-butyllithium or sodium hydride.

The intermediate (If) is readily available or is synthesized by conventional methods.

The present invention also provides novel intermediates of formula

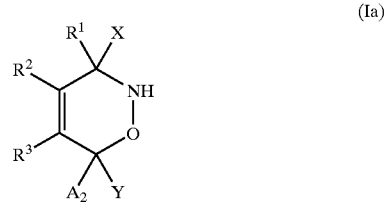
(Ia)

wherein A₁, A₂, R¹, R²₁, R³, X and Y have the values defined above.

It will be appreciated that the production of compounds of formula (I) and any novel intermediates, may be optionally followed by the formation of esters or salts thereof.

According to a further aspect of the invention the compounds described above have pharmaceutical activity. They have been shown to possess affinity for glutamate receptors.

Excitatory amino acid or glutamate receptors are subdivided into two types, ionotropic and metabotropic. Ionotropic glutamate receptors are ligand gated ion channels that are composed of multiple subunit proteins forming multimeric complexes. Ionotropic glutamate receptors are selectively activated by the agonists N-methyl-D-aspartate, AMPA, and kainate (Sommer B. and Seeburg P. H., Trends Pharmacol. Sci. 13: 291–296, 1993). Metabotropic glutamate receptors are a family of G-protein coupled receptors which are coupled to increases in phosphoinositide hydrolysis and decreases in cAMP formation. (Schoepp D. D. and Conn J. P., Trends Pharmacol. Sci. 14: 13–20, 1993).

The compounds of the present invention are active in a screen for activity in metabotropic receptors as described in Kingston et al, Neuropharmacology 1995, 34, 887–894. They have been shown to possess affinity for group 1 metabotropic receptors, especially mnGluR1 receptors. They are particularly useful as selective mGluR1 antagonists.

The compounds of the invention are thus indicated for use in the treatment of disorders of the central nervous system such as cognitive impairment and acute neurodegenerative diseases, for example stroke, cerebral ischaemia and head and spinal cord trauma, and chronic neurodegenerative diseases such as, for example, Alzheimer's disease, Parkinson's disease, Amyotropic lateral sclerosis, AIDS-induced dementia and Huntington,s Chorea. The compounds are also indicated for use as antipsychotic, anti-emetic agents and as anticonvulsant agents, for example in the treatment of epilepsy. They are also of potential use as anxiolytic and antidepressant agents. The compounds are also indicated for use as analgesics, especially for the treatment of acute and chronic pain conditions associated with inflammation, cancer surgery and migraine.

The present invention also provides the use of a selective mnGluR1 antagonist for the manufacture of a medicament for the treatment of migraine. The selective mnGluR1 antagonist is preferably at least 10 fold selective for mGlur1 over mGluR5, more preferably at least 100 fold selective. The present invention also provides the use of a compound of formula (I) or formula (II) or a pharmaceutically-acceptable salt or ester thereof, for the manufacture of a medicament for the treatment of migraine.

The present invention further provides the use of a compound of formula (I) or formula (II) or a pharmaceutically-acceptable salt or ester thereof, for the manufacture of a medicament for the treatment of pain associated with migraine.

The ability of test compounds go treat migraine may be demonstrated as described in U.S. Pat. No. 5,817,671 (Oct. 6, 1998) U.S. Pat. No. 5,792,763 (Aug. 11, 1998) and J. Neurosci, Methods (1998), 81 (1, 2) 19–24.

The compound of Example 5, 3,6-Dihydro-3,5-dimethyl-6-(4-ethoxyphenyl)-2-(4-methylcarbamoylbenzenesulphonyl)-2H-1,2-oxazine, has been found particularly effective.

In the method of invention the compounds are preferably administered in a pharmaceutical formulation comprising a pharmaceutically-acceptable diluent or carrier in association with a compound of formula (I), or a pharmaceutically-acceptable salt thereof.

The compounds may be administered by various routes, for example, by the oral or rectal route, topically or parenterally, for example by injection, and are usually employed in the form of a pharmaceutical composition. Such compositions form part of the present invention and are prepared in a manner well known in the pharmaceutical art and normally comprise at least one active compound in association with a pharmaceutically-acceptable diluent or carrier. In making the compositions of the present invention, the active ingredient will usually be mixed with a carrier, or diluted by a carrier, and/or enclosed with a carrier which may, for example, be in the form of a capsule, sachet, paper or other container. Where the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, as a solid or in a liquid medium, ointments containing, for example, up to 10% by weight of the active compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydroxybenzoate, talc, magnesium stearate and mineral oil. Compositions in injectable form may, as it is well known in the art, be formulated so as to provide quick, sustained or delayed release of the active ingredient after administration to the patient.

When the compositions are formulated in unit dosage form, it is preferred that each unit dosage form contains from 5 mg to 500 mg, for example, from 15 mg to 200 mg. The term 'unit dosage form' refers to physically discrete units suitable as unit dosages for human subjects and animals. Each unit contains a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances, including the condition to be treated, the choice of compound to be administered and the chosen route of administration, and therefore the above dosage ranges are not intended to limit the scope of the invention in any way.

The invention is illustrated by the following Examples.

EXAMPLE 1

2-(4-Acetamidobenzenesulphonyl)-3,6-dihydro-3,5-dimethyl-6-(4-methoxyphenyl)-2H-1,2-oxazine.

i) A suspension of 4-methoxybenzaldehyde (10 g, 0.073 mol) and α-formylethylidenetriphenylphosphorane (25.7 g, 0.081 mol) in dried toluene (200 ml) was heated with stirring at reflux under an atmosphere of nitrogen for 24 h. The cooled reaction mixture was decanted to removed insoluble material and evaporated to give a brown oil. The oil was taken up in diethylether and the resulting suspension purified on flash silica eluting with hexane-diethyl ether (3:2). The resulting oil was a mixture of required product and 4-methoxybenzaldehyde and therefore dissolved in dried toluene (150 ml) and reaction continued as described above with α-formylethylidenetriphenylphosphorane (5.76 g, 0.018 ml) for 7 h. Following the work up and chromatography as above 3-(4-methoxyphenyl)-2-methylpropenaldehyde was obtained as a yellow oil.

ii) To a solution of 3-(4-methoxyphenyl)-2-methylpropenaldehyde (10.3 g, 0.058 mol) in dried diethyl ether (150 ml) cooled to −15° C. and stirred under an atmosphere of nitrogen was added a solution of ethylmagnesium bromide in diethylether (3M, 21.4 ml). The reaction mixture was allowed to warm to room temperature and after ½ hour poured onto ice cold aqueous hydrochloric acid (2M, 50 ml). The organic phase was separated, washed with water, a saturated solution of sodium bicarbonate and brine. The organic phase was dried over magnesium sulphate, filtered and evaporated to give 3-hydroxy-1-(4-methoxyphenyl)-2-methylpent-1-ene as a yellow oil.

iii) A mixture of 3-hydroxy-1-(4-methoxyphenyl)-2-methylpent-1-ene (11.88 g, 0.058 mol), potassium hydrogen sulphate (0.78 g, 5.7 mmol) and hydroquinone (0.01 g) was heated with stirring at 105° C. under vacuum (4 mbar) for ½ hour. The temperature of the reaction mixture was then raised and 1-(4-methoxyphenyl)-2-methylpent-1E, 3E-diene collected by distillation as an oil which crystallised on standing.

iv) To a solution of 1-chloro-1-nitrosocyclohexane (4.13 g, 28.07 mmol) in ethanol (4 ml) and diethylether (8 ml) cooled in an ice bath was added a solution of 1-(4-methoxyphenyl)-2-methylpent-1E, 3E-diene (4.4 g, 23.4 mmol) in diethylether (4 ml). The reaction vessel was sealed and stood at 0° C. for 3 days, the resulting crystals were filtered and washed with diethylether to give 3,6-dihydro-3,5-dimethyl-6-(4-methoxyphenyl)-2H-1,2-oxazine hydrochloride.

v) To a stirred suspension of 4-N-acetylsulphanilyl chloride (2.7 g, 11.55 mmol) and triethylamine (1.95 g, 19.25 mmol) in dichloromethane (50 ml) was added portionwise solid 3,6-dihydro-3,5-dimethyl-6-(4-methoxyphenyl)-2H-1,2-oxazine hydrochloride (1.97 g, 7.70 mmol). The resulting solution was stirred at room temperature for 5 h then washed with water three times, aqueous sodium hydroxide (2M), water and brine. The organic phase was dried over magnesium sulphate, filtered and evaporated, the resulting foam was purified on flash silica eluting with ethylacetate-hexane (3:2) to give 2-(4-acetamidobenzenesulphonyl)-3,6-dihydro-3,5-dimethyl-6-(4-methoxyphenyl)-2H-1,2-oxazine as a white foam. $^1$H NMR (CDCl$_3$) δ 1.39(3H,s), 1.41(3H, d), 2.20(3H, s), 3.79(3H, s), 4.45(1H, m), 5.19(1H, s), 5.68(1H, d), 6.80(2H, d), 7.13(2H, d), 7.57(1H, bs), 7.59(2H, d), 7.80(2H, d).

The following compounds were made by a similar method. 2-(4-Acetamidobenzenesulphonyl)-3,6-dihydro-6-(4-methoxyphenyl)-5-methyl-2H-1,2-oxazine. $^1$H NMR (CDCl$_3$)

δ 1.28(3H, s), 1.33(3H, d), 3.74(3H, s), 4.23(1H, m), 5.12(1H, br, s), 5.71(1H, m), 6.03(2H, br, s), 6.60(2H, d), 6.93(2H, d), 7.17(2H, d), 7.46(2H, d).

2-(4-Acetamidobenzenesulphonyl)-3,6-dihydro-5-ethyl-6-(4-methoxyphenyl)-3-methyl-2H-1,2-oxazine.

2-(4-Acetamidobenzenesulphonyl)-3,6-dihydro-5-methyl-6-phenyl-2H-1,2-oxazine.

2-(4-Acetamidobenzenesulphonyl)-3,6-dihydro-6-(4-ethoxyphenyl)-5-ethyl-2H-1,2-oxazine.

2-(4-Acetamidobenzenesulphonyl)-3,6-dihydro-6-(4-ethoxy phenyl)-5-methyl-2H-1,2-oxazine.

EXAMPLE 2

2-(4-Acetamidobenzenesulphonyl)-3,6-dihydro-3,5-dimethyl-6-(4-ethoxyphenyl)-2H-1,2-oxazine.

i) A suspension of 4-ethoxybenzaldehyde (20 g, 0.133 mol) and α-formylethylidenetriphenylphosphorane (46.6 g, 0.146 mol) in dried toluene (400 ml) was heated with stirring at reflux under an atmosphere of nitrogen for 40 h. The mixture was cooled, diethyl ether added and filtered through a pad of celite. The filtrate was evaporated and the residue taken up in diethyl e;her and the resulting suspension purified on flash silica eluting with hexane-diethyl ether (4:1). The resulting oil was crystallised from hexane-diethyl ether to give 3-(4-ethoxyphenyl)-2-methylpropenaldehyde as yellow crystals.

ii) To a solution of 3-(4-ethoxyphenyl)-2-methylpropenaldehyde (10 g, 0.053 mol) in dried diethyl ether (150 ml) cooled to −15° C. and stirred under an atmosphere of nitrogen was added a solution of ethylmagnesium bromide in diethylether (3M, 19.3 ml) The reaction mixture was allowed to warm to room temperature and after ½ h poured onto ice cold aqueous hydrochloric acid (2M, 50 ml) and the organic phase washed with water and brine. The organic phase was dried over magnesium sulphate, filtered and evaporated to give 1-(4-ethoxyphenyl)-3-hydroxy-2-methylpent-1-ene as a colourless oil.

iii) A mixture of 1-(4-ethoxyphenyl)-3-hydroxy-2-methylpent-1-ene (11.14 g, 0.051 mol), potassium hydrogen sulphate (0.70 g, 5.1 mmol) and hydroquinone (0.01 g) was heated with stirring at 100° C. under vacuum (4 mbar) for ½h. 1-(4-Ethoxyphenyl)-2-methylpent-1E,3E-diene was then collected by distillation at 0.6 mbar/96° C.

iv) To a solution of 1-chloro-1-nitrosocyclohexane (3.22 g, 21.86 mmol) in ethanol (2.31 ml) and diethyl ether (8 ml) cooled in an ice bath was added a solution of 1-(4-ethoxyphenyl)-2-methylpent-1E,3E-diene (4.0 g, 19.88 mmol) in diethyl ether (4 ml). The reaction vessel was sealed and kept in a fridge at 0° C. over a period of 4 weeks yielding three crops of 3,6-dihydro-3,5-dimethyl-6-(4-ethoxyphenyl)-2H-1,2-oxazine hydrochloride as white crystals.

v) To a stirred suspension of 4-N-acetylsulphanilyl chloride (1.14 g, 4.9 mmol) and triethylamine (0.82 g, 8.15 mmol) in dichloromethane (15 ml) was added a solution of 3,6-dihydro-3,5-dimethyl-6-(4-ethoxyphenyl)-2H-1,2-oxazine hydrochloride (0.88 g, 3.26 mmol) in dichloromethane (15 ml). The resulting solution was stirred at room temperature for 8 h then washed with water three times, aqueous sodium hydroxide (2M), water and brine. The organic phase was dried over magnesium sulphate, filtered and evaporated to a foam. The crude product was purified on flash silica eluting with ethylacetate-hexane (3:2) to give 2-(4-acetamidobenzenesulphonyl)-3,6-dihydro-3,5-dimethyl-6-(4-ethoxyphenyl)-2H-1,2-oxazine as a white foam. $^1$H NMR (CDCl$_3$) δ 1.41(9H, m), 2.14(3H, s), 4.01(2H, q), 4.43(1H, m), 5.17(1H, s), 5.66(1H, d), 6.79(2H, d), 7.11(2H, d), 7.60(2H, d), 7.79(2H, d), 7.89(1H, bs).

EXAMPLE 2

Method 2 i) A solution of t-butyl N-hydroxycarbamate (11.14 g, 84 mmol) in dichloromethane (300 ml) was added dropwise over 25 mins to a stirred mixture of 1-(4-ethoxyphenyl)-2-methyl-pent-1E,3E-diene (8.46 g, 42 mmol) and tetrabutylammonium periodate (32.6 g, 75 mmol) in dichloromethane (300 ml) cooled to 4° C. under nitrogen atmosphere. After stirring for 4 h at 3–4° C. the reaction mixture was washed with 2M aqueous sodium carbonate containing sodium metabisulphite and then twice with water. The dichloromethane solution was dried over magnesium sulphate, filtered and evaporated to an oil (33.1 g). This was purified by chromatography twice on silica eluting with n-hexane: diethyl ether 4:1 to give 2-t-butoxycarbonyl-3,6-dihydro-3,5-dimethyl-6-(4-ethoxyphenyl)-2H-1,2-oxazine as a yellow oil.

ii) Acetyl chloride (30 ml) was added dropwise over 10 mins to a cooled solution of methanol (300 ml) The resulting solution of hydrogen chloride in methanol was added to a stirred solution of 2-t-butoxycarbonyl-3, 6-dihydro-3,5-dimethyl-6-(4-ethoxyphenyl)-2H-1, 2-oxazine (11.6 g, 34.8 mmol) in methanol (50 ml). After 4 h at room temperature the mixture was evaporated to a solid (8.35 g), triturated with diethyl ether and the solid filtered to give 3,6-dihydro-3,5-dimethyl-6-(4-ethoxyphenyl)-2H-1,2-oxazine hydrochloride.

iii) The 3,6-dihydro-3,5-dimethyl-6-(4-ethoxyphenyl)-2H-1,2-oxazine hydrochloride was reacted with 4-N-acetylsulphamidyl chloride as described in Example 2 Method 1 to give 2-(4-acetamidobenzenesulphonyl)-3, 6-dihydro-3,5-dimethyl-6-(4-ethoxyphenyl)-2H-1,2-oxazine.

EXAMPLE 3

2-(4-aminobenzenesulphonyl) -3,6-dihydro-3,5-dimethyl-6-(4-thoxyphenyl)-2H-1,2-oxazine.

i) A stirred mixture of 2-(4-acetamidobenzenesulphonyl)-3, 6-dihydro-3,5-dimethyl-6-(4-ethoxyphenyl) -2H-1, 2-oxazine (0.153 g) and powdered potassium hydroxide (40mg) in methanol (5 ml) was-heated under reflux for 24 h. The cooled mixture was diluted with dichloromethane and the solution washed with water. The dichloromethane solution was separated, dried over magnesium sulphate, filtered and evaporated to dryness. The residual oil was purified by chromatography on silica using ethyl acetate:n-hexane 3:2 as eluant to give 2-(4-aminobenzenesulphonyl)-3,6-dihydro-3,5-dimethyl-6-(4-ethoxyphenyl)-2H-1,2-oxazine as a colourless foam. $^1$H NMR (CDCl$_3$) δ 1.44(9H, m), 4.02(2H, q), 4.13(2H, br s), 4.44 (1H, m), 5.02(1H, br s), 5.70(1H, m), 6.61(2H, d), 6.83(2H, d), 7.13(2H, d), 7.65(2H, d).

The following compounds were made by a similar method.

2-(4-Aminobenzenesulphonyl)-3,6-dihydro-3,5-dimethyl-6-(4-methoxyphenyl)-2H-1,2-oxazine. $^1$H NMR (CDCl$_3$) δ 1.28(3H, s), 1.33(3H, d), 3.74(3H, s), 4.23(1H, m), 5.12(1H, br, s), 5.71(1H, m), 6.03(2H, br, s), 6.60(2H, d), 6.93(2H, d), 7.17(2H, d), 7.46(2H, d)

2-(4-Aminobenzenesulphonyl)-3,6-dihydro-5-ethyl-6-(4-methoxyphenyl)-2H-1,2-oxazine.

2-(4-Aminobenzenesulphonyl)-3,6-dihydro-5-ethyl-3-methyl-6-(4-methoxyphenyl)-2H-1,2-oxazine.

EXAMPLE 4

3,6-Dihydro-3,5-dimethyl-6(4-ethoxyphenyl)-2-(4-ethanesulphonamidophenyl)sulphonyl-2H-1,2-oxazine.

i) A solution of methanesulphonyl chloride (36 mg, 0.31 mmol) in dichloromethane (0.24 ml) was added dropwise over 5 min to a stirred solution of 2-(4-aminobenzenesulphonyl)-3,6-dihydro-3,5-dimethyl-6-(4-ethoxyphenyl)-2H-1,2-oxazine (0.10 g, 0.26 mmol) and triethylamine (37 mg, 0.36 mmol) in dichloromethane (4 ml) under nitrogen atmosphere. After 3 h at room temperature extra triethylamine (37 mg) and methanesulphonyl chloride (36 mg) were added. After a further 1h the mixture was diluted with water (5 ml) and stirred vigorously for ½ h. The dichloromethane solution was separated, dried, filtered and evaporated to a brown oil (0.17 g). This was purified by chromatography on silica eluting with dichloromethane:diethyl ether 19:1 to give 3,6-dihydro-3,5-dimethyl-6-(4-ethoxyphenyl)-2-[4-bis(methane-sulphonyl)amidophenyl)-2H-1,2-oxazine as a foam.

ii) The bis(methanesulphonyl)amide (50 mg) was dissolved in methanol(0.5 ml) and 2M sodium hydroxide (0.1 ml) at room temperature. After 3 h stirring the mixture was diluted with water (1.2 ml) and 2M hydrochloric acid (0.2 ml) and extracted with dichloromethane (2×1 ml). The extracts were dried, filtered and evaporated. The residue was purified by chromatography on silica eluting with dichloromethane:diethyl ether 4:1 to give 3,6-Dihydro-3,5-dimethyl-6(4-ethoxyphenyl)-2-(4-methanesulphonamidophenyl)sulphonyl-2H-1,2-oxazine as a colourless foam. $^1$H NMR (CDCl$_3$)δ 1.46(9H, m), 3.10(3H, s), 4.04(2H, q), 44.50(1H, m), 5.15(1H, br, s), 5.71(1H, m), 6.76(1H, br, s), 6.83(2H, d), 7.11(2H, d), 7.20(2H, d), 7.84(2H, d)

The following compound was made by a similar method.

2-(4-[4-Acetamidophenyl)sulphonamido]benzenesulphonyl)-3,6-dihydro-3,5-dimethyl-6-(4-methoxyphenyl)-2H-1,2-oxazine.

EXAMPLE 5

Method 1

3,6-Dihydro-3,5-dimethyl-6-(4-ethoxyphenyl)-2-(4-methylcarbamoylbenzenesulphonyl)-2H-1,2-oxazine.

A solution of methyl chloroformate (0.1 g) was added to a stirred mixture of 2-(4-aminobenzenesulphonyl)-3,6-dihydro-3,5-dimethyl-6-(4-ethoxyphenyl)-2H-1,2-oxazine (80 mg) and 4-(dimethylamino)pyridine (94 mg) in chloroform (1.3ml). After 3 days at 40° C., the reaction solution was diluted with chloroform (3 ml) and chromatographed directly on silica eluting with dichloromethane:diethyl ether 19:1 to give 3,6-dihydro-3,5-dimethyl-6-(4-ethoxyphenyl)-2-(4-methylcarbamoylbenzenesulphonyl)-2H-1,2-oxazine as a glassy solid. $^1$H NMR (CDCl$_3$) δ 1.43(9H, m), 3.82(3H, s), 4.03(2H, q), 4.48(1H, m), 5.20(1H, br s), 6.80(1H, br s), 6.83(2H, d), 7.12(2H, d) 7.47(2H, d), 7.82(2H, d).

Method 2 i) Chlorosulphonic acid (2.4 ml) followed by thionyl chloride (7.5 ml) were added to a stirred solution of methyl N-phenyl-carbamate (5.0 g, 33 mmol) and dimethylformamide (2.5 ml) cooled in an ice bath under nitrogen atmosphere. After 1.5 h the reaction mixture was filtered to remove solid and washed with dichloromethane. The filtrate was evaporated to dryness in vacuum (45° C. @ 1 mmhg) and the residue (7.0 g) chromatographed on silica eluting with ethyl acetate to give an oil (2.6 g). This was redissolved in dichloromethane, filtered and the filtrate evaporated to give N-carbomethoxvsulfanilyl chloride.

ii) Triethylamine (1.3 ml) followed by a solution of 3,6-dihydro-2,5-dimethyl-6-(4-ethoxyphenyl)-2H-1,2-oxazine hydrochloride (1.0 g, 3.7 mmol) in dried dichloromethane (15 ml) were added to a stirred mixture of N-carbomethoxysulfanilyl chloride (1.3 g, 5.56 mmol) in dichloromethane (15 ml). After 15 h at room temperature the reaction mixture was washed with water and then stirred overnight with 2M sodium hydroxide to remove excess of the sulfanilyl chloride. The dichloromethane solution was dried over magnesium sulphate, filtered and evaporated to a white solid foam. This was purified by chromatography on silica eluting with dichloromethane:diethyl ether 19:1 to give 3,6-dihydro-3,5-dimethyl-6-(4-ethoxyphenyl)-2-(4-methylcarbamoylbenzenesulphonyl)-2H-1,2-oxazine as a solid foam.

EXAMPLE 6

2-(4-Acetamidobenzenesulphonyl)-3,6-dihydro-6-(4-ethoxyphenyl)-3-hydroxymethyl-5-methyl-2H-1,2-oxazine.

i) To a stirred suspension of 2-hydroxyethyltriphenylphosphonium bromide (30 g, 0.077 mol) in dried tetrahydrofuran (300 ml) cooled to −40° C. under an atmosphere of nitrogen was added a solution of n-butyllithium in hexane (2.5M, 58.5 ml) dropwise. The resulting orange suspension was then stirred at 50° C. with occasional ultrasonication for 3 h, cooled to −60° C. and a solution of 3-(4-ethoxyphenyl)-2-methylpropenaldehyde (7.4 g, 0.039 ml) in dried tetrahydrofuran (25 ml) added dropwise and allowed to warm to 0° C. After ½ h, water was added and the organic phase separated. The aqueous phase was extracted with diethyl ether and the combined organic phases washed four times with water and then brine. The organic phase was dried over magnesium sulphate, filtered and evaporated to an oil. The oil was dissolved in a minimum of diethyl ether and chromatographed on flash silica eluting with hexane then hexane-diethyl ether (3:2) to give 5-(4-ethoxyphenyl)-4-methylpent-2E,4E-dienal as a white solid.

ii) To a stirred solution of 5-(4-ethoxyphenyl)-4-methylpent-2E,4E-dienal (1.55 g, 7.10 mmol) and tetrabutylammonium periodate (5.54 g, 12.78 mml) in dichloromethane (30 ml) cooled to 0° C. for 2 h and then washed with aqueous sodium carbonate mixed with sodium metabisulphate, two times with water and brine. The organic phase was dried over magnesium sulphate, filtered and evaporated to give an oil. The crude product was purified on flash silica eluting with diethyl ether-hexane (16:9) to give 2-t-butyloxycarbonyl-3,6-dihydro-6-(4-ethoxyphenyl)-3-hydroxymethyl-5-methyl-2H-1,2-oxazine as a colourless oil.

ii) A solution of 2-t-butyloxycarbonyl-3,6-dihydro-6-(4-ethoxyphenyl)-3-hydroxymethyl-5-methyl-2H-1,2-oxazine (2.02 g, 5.78 mmol) in methanol (10 ml) saturated with hydrogen chloride gas was stirred at room temperature for 2 h. The solvent was evaporated and the residue crystallised from methanol-diethyl ether to give 3,6-dihydro-6-(4-ethoxyphenyl)-3-hydroxymethyl-5-methyl-2H-1,2-oxazine hydrochloride as a crystalline product.

iv) To a stirred solution of 3,6-dihydro-6-(4-ethoxyphenyl)-3-hydroxymethyl-5-methyl-2H-1,2-oxazine hydrochloride (1.31 g, 4.59 mmol) and triethylamine (1.34 ml, 9.63 mmol) in dichloromethane (50 ml) was added 4-N-acetylsulphanilyl chloride (1.07 g, 4.59 mmol). After 4 h at room temperature, the reaction mixture was washed twice with water and brine. The organic phase was dried over magnesium sulphate, filtered and evaporated to a foam, purified on flash silica eluting with ethylacetate to give 2-(4-acetamidobenzenesulphonyl)-3,6-dihydro-6-(4-ethoxyphenyl)-3-hydroxymethyl-5-methyl-2H-1,2-oxazine as a white foam. $^1$H NMR (CDCl$_3$)δ 1.39(3H, t), 2.21(3H, s), 3.85(2H, m), 4.00(2H, q), 4.54(1H, m), 5.32(1H, s), 5.70(1H, m), 6.80(2H, d), 7.09(2H, d), 7.54(1H, bs) 7.63(2H, d), 7.85(2H, d).

EXAMPLKE 7

2-(4-Acetamidobenzenesulphonyl)-3-carboxy-3,6-dihydro-6-(4-ethoxyphenyl)-5-methyl-2H-1,2-oxazine.

To a stirred solution of 2-(4-acetamidobenzenesulphonyl)-3,6-dihydro-6-(4-ethoxyphenyl)-3-hydroxymethyl-5-methyl-2H-1,2-oxazine (1.02 g, 2.28 mmol) in acetone (20 ml) at 10° C. was added a solution of aaueous chromic acid (8M, 1.2 ml) dropwise. Stirred at room temperature for 2.5 h with addition of aqueous chromic acid (8M, 1.2 ml and 0.4ml) at intervals. Aqueous sodium metabisulphite was then added to terminate the reaction and the mixture concentrated in vacuo. The concentrate was diluted with water and extracted twice with ethyl acetate. The combined extracts was washed with water and brine, dried over magnesium sulphate, filtered and evaporated to a foam. 2-(4-Acetamidobenzenesulphonyl)-3-carboxy-3,6-dihydro-6-(4-ethoxyphenyl)-5-methyl-2H-1,2-oxazine crystallised as a white power from chloroform. $^1$H NMR (CDCl$_3$)δ 1.40(3H, t) 1.48(3H, s), 2.15(2H, s), 4.01 (2H, q), 4.97(1H, d), 5.29(1H, s), 5.85(1H, d), 6.75(2H, d), 7.19(2H, d), 7.68(2H, d), 7.22(2H, d).

EXAMPLE 8

2-(4-Acetamidobenzenesulphonyl)-3,6-dihydro-6-(4-ethoxyphenyl)-3-methoxycarbonyl-5-methyl-2H-1,2-oxazine.

To a stirred solution of 2-(acetamidobenzenesulphonyl)-3-carboxy-3,6-dihydro-6-(4-ethoxyphenyl)-5-methyl-2H-1,2-oxazine (100 mg, 0.22 mmol) in ethyl acetate (15 ml) cooled to 5° C. was added a solution of diazomethane in diethyl ether dropwise at intervals over a period of ½ h until all starting material had been consumed. Acetic acid was added and the reaction mixture washed with a saturated solution of sodium bicarbonate, two times with water and brine. The organic phase was dried over magnesium sulphate, filtered and evaporated to an oil. The crude oil was purified on flash silica eluting with diethyl ether and then diethyl ether-ethyl acetate (4:1) to give 2-(4-acetamidobenzenesulphonyl)-3,6-dihydro-6-(4-ethoxyphenyl)-3-methoxycarbonyl-5-methyl-2H-1,2-oxazine as a white foam. $^1$H NMR (CDCl$_3$) δ 1.38(3H, t), 2.20(3H, s), 3.86(3H, s) 3.99 (2H, q), 5.05(1H, m), 5.33(1H, s), 5.80(1H, d), 5.79(2H, d), 7.14(2H, d), 7.66(2H, d), 7.79(2H, d).

EXAMPLE 9

3,6-Dihydro-3,5-dimethyl-6-(4-methoxyphenyl)-2-(3-methyl benzenesulphonyl)-2H-1,2-oxazine.

To a solution of 3-methylbenzenesulphonyl chloride (0.075 mmol) in acetonitrile (1.5 ml) was added a solution of 3,6-dihydro-3,5-dimethyl-6-(4-methoxyphenyl)-2H-1,2-oxazine hydrochloride(0.403 mmol) in chloroform (0.5 ml) followed by poly(4-vinyl)pyridine (53 mg). The mixture was shaken at room temperature for 24 h then added polystyrene (co-divinylbenzene)amino methylated (100 mg) and the mixture shaken at room temperature for a further 24 h. The mixture was then filtered and the resin washed twice with chloroform. The filtrate was evaporated to give 3,6-dihydro-3,5-dimethyl-6-(4-methoxyphenyl)-2-(3-methylbenzenesulphonyl)-2H-1,2-oxazine as an oil. $^1$H NMR (CDCl$_3$)δ 1.56(3H, d), 2.39(3H, s), 3.82(3H, s) 4.49 (1H, m), 5.20(1H, s), 5.69(1H, d), 6.81(2H, d), 7.11(2H, d), 7.34(2H, m), 7.67(2H, d)

The following compounds were made by a similar method.

3,6-Dihydro-3,5-dimethyl-2-(4-fluorobenzenesulphonyl)-6-(4-methoxyphenyl)-2H-1,2-oxazine. $^1$H NMR (CDCl$_3$)δ 1.44(3H, d), 1.53(3H, s), 3.80(2H, s), 4.48(1H, m), 5.18(1H, s), 5.70(1H, d), 6.82(2H, d), 7.10(2H, d), 7.88(4H, m)

2-Benzenesulphonyl-3,6-dihydro-3,5-dimethyl-6-(4-methoxyyphenyl)-2H-1,2-oxazine. $^1$H NMR (CDCl$_3$)δ 1.45a(3H, d) 3.80(3H, s), 4.51(1H, m) 5.21 (1H, s) 5.70(1H, m), 6.84(2H, d) 7.11 (2H, d) 7.44(2H, m) 7.56 (1H, m), 7.88 (2H, d).

2-(4–Cyanobenzenesulphonyl-3,6-dihydro-3,5-dimethyl-6-(4-methoxyphenyl)-2H-1,2-oxazine. $^1$H NMR (CDCl$_3$)δ 1.53 (3H, d), 3.82 (3H, s), 4.52 (1H, m), 5.19 (1H, s), 5.70(1H, d), 6.84(2H, d), 7.07(2H, d), 7.71(2H, d), 7.92(2H, d), 2-(4-Bromobenzenesulphonyl -3,5-dimethyl-6-(4-methoxyphenyl)-2H-1,2-oxazine. $^1$H NMR (CDCl$_3$) δ 1.43(3H, d), 3.83(3H, s), 4.48(1H, m), 5.17(1H, s) 5.70(1H, d), 6.80(2H, d), 7.08(2H, d), 7.55(2H, d), 7.67(2H, d).

EXAMPLE 10

2-(4-Acetamidbenzensulphonyl)-5-methyl-6-(4-methoxyphenyl)-3,4,5,6-tetrahydro-2H-1,2-oxazine.

A solution of 2-(4-acetamidobenzenesulphonyl)-3,6-dihydro-5-methyl-6-(4-methoxyphenyl)-2H-1,2-oxazine (90 mg, 0.22 mmol) in ethanol (3 ml) was shaken with 10% palladium on carbon (60 mg) under hydrogen atmosphere at 60 psi for 7 h. The reaction mixture was regularly monitored by HPLC. to avoid over-reduction of the oxazine N—O bond. The mixture. was filtered and the filtrate evaporated. The residue was chromatographed on silica eluting with dichloromethane:diethyl ether 9:1 to give the title product as a white solid foam (60 mg, 67%). HPLC. using KR100-5C18 column with 60% acetonitrile: 40% water: 0.2% ammonia showed two diastereomeric products ratio 42:58 with retention times 8.7 and 9.3 minutes.

EXAMPLE 11

3,5-Dimethyl-2-(4-methoxybenzoyl)-6-(4-methoxyphenyl)-3,6-dihydro-2H-1,2-oxazine.

A mixture of 0.75 ml of a 0.05M solution of 3,5-dimethyl-6-(4-methoxyphenyl)-3,6-dihydro-2H-1,2-oxazine in dichloromethane, 0.5 ml of a 0.05M solution of 4-methoxybenzoic acid in dimethylformamide, and 0.5 ml of a 0.075M solution of N-ethyl-N'-dimethylaminopropyl-carbodiimide hydrochloroide in acetonitrile was stirred at ambient temperature for 18 h. Methanol (1 ml) was added with stirring and the mixture applied to a methanol washed 500 mg Isolute SCX cartridge (Jones Chromatography). The absorbent was then washed with methanol (2.5 ml) and the combined run through and washing concentrated to dryness using a centrifugal evaporator. The residue was dissolved in ethyl acetate (0.5 ml) and applied to a 100 mg Isolute SI cartridge (Jones Chromatography). Elution with ethyl acetate (2 ml) followed by removal of the solvent by centrifugal evaporation gave 3,5-dimethyl-2-(4-methoxybenzoyl)-6-(4-methoxyphenyl)-3,6-dihydro-2H-1,2-oxazine.

The following compounds were made by a similar method.

3,5-Dimethyl-2-(4-chlorobenzoyl)-6-(4-methoxyphenyl)-3,6-dihydro-2H-1,2-oxazine.

3,5-Dimethyl-2-(4-fluorobenzoyl)-6-(4-methoxyphenyl)-3,6-dihydro-2H-1,2-oxazine. $^1$H NMR (CDCl$_3$)δ 1.40 (3H, s), 1.51(3H, d), 3.80(3H, s), 5.08(2H, m), 5.80 (1H, d), 6.87 (2H, d), 7.04(2H, t), 7.12(2H, d), 7.81(2H, dd).

EXAMPLE 12

3,5-Dimethyl-2-(3,4-dimethoxybenzyl)-6-(4-methoxyphenyl)-3,6-dihydro-2H-1,2-oxazine.

A mixture of 0.5 ml of a 0.05M solution of 3,5-dimethyl-6-(4-methoxyphenyl)-3,6-dihydro-2H-1,2-oxazine in dichloromethane. 0.5 ml of a 0.75M solution of 3,4-dimethoxybenzaldehyde in dichloromethane, and 0.5 ml of a 0.75M solution of sodium triacetoxyborohydride in dichloromethane was stirred at ambient temperature for 19 h. Methanol (1.0 ml) was added with stirring and the mixture applied to a methanol washed 500 mg Isolute SCX cartridge (Jones Chromatography). The absorbent was washed with methanol (2.5 ml) and then eluted with 2M ammonia in methanol (2.5 ml). The eluate was concentrated to dryness using a centrifugal evaporator and the residue dissolved in chloroform (2 ml) and added to methylisocyanate-polystyrene (loading 1.0 meq/g, 100 mg). This suspension was shaken gently for 19 h, then filtered and resin washed with chloroform (2×2 ml). Removal of the solvent from the combined filtrates by centrifugal evaporation gave 3,5-dimethyl-2-(3,4-dimethoxybenzyl)-6-(4-methoxyphenyl)-3,6-dihydro-2H-1,2-oxazine. $^1$H NMR (CDCl$_3$) δ 1.23(3H, d), 1.49(3H, s), 3.39(1H, m), 3.62(1H, d), 3.70(3H, s), 3.79(3H, s), 3.83(3H, s), 4.05(1H, d), 4.92(1H, s), 5.61 (1H, d), 6.64 (3 H, m),6.81 (2H, d), 7.22 (2H, d).

The following compounds were made by a similar method.

3,5-Dimethyl-2-(4-nitrobenzyl)-6-(4-methoxyphenyl)-3,6-dihydro-2H-1,2-oxazine. 1H NMR (CDCl$_3$)δ 1.26 (3H, d), 1.58(3H, s), 3.44(1H, m), 3.64(1H, d), 3.85 (3H, s), 4.13(1H, d), 4.85(1H, s), 5.62(1H, bs), 6.81 (2H, d), 7.02(2H, d), 7.16(2H, d), 7.88(2H, d).

EXAMPLE 13

Tablet

A tablet is prepared using the ingredients below:

| | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

EXAMPLE 14

Tablet

Tablets each containing 60 mg of active ingredient are made as follows:

| | |
|---|---|
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

EXAMPLE 15

Capsules

Capsules each containing 80 mg medicament are made as follows:

| Active Ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

EXAMPLE 16

Suspensions each containing 50 mg of medicament per 5 ml dose are made as follows:

| Active Ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

What is claimed is:

1. A method of treating an animal, including a human, suffering from or susceptible to a condition indicating the administration of a selective mGluR1 antagonist which method comprises administering a compound of the formula

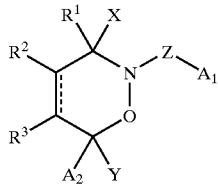

in which, $R^1$, $R^2$ and $R^3$ are independently hydrogen, $(C_1-C_6)$alkyl, $(C_2-C_6)$alkenyl, $(C_3-C_{10})$cycloalkyl, unsubstituted or substituted aryl, unsubstituted or substituted aryl$(C_1-C_6)$alkyl, unsubstituted or substituted aryl$(C_2-C_6)$alkenyl, halo, carboxy, $(C_{1-C6})$alkoxycarbonyl or $-(CH_2)_m-OH$, wherein m is 1, 2 or 3;

- - - indicates a single or a double bond;

X and Y are each independently hydrogen, or X and Y together represent a bridge of the formula $-(CH_2)n-$, where n is 1 or 2;

$A_1$ and $A_2$ are each independently an unsubstituted or substituted aryl; Z is $-CO-$, $-SO_2-$ or $-CH_2-$;

provided that, when Z is $-CO-$, $A_1$ is not 3,4,5-trimethoxyphenyl;

or a pharmaceutically-acceptable salt or ester thereof.

2. A method of treating an animal, including a human, suffering from or susceptible to migraine, which method comprises administering a compound of the formula

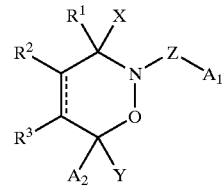

in which, $R^1$, $R^2$, and $R^3$ are independently hydrogen, $(C_1-C_6)$alkyl, $(C_2-C_6)$alkenyl, $(C_3-C_{10})$cycloalkyl, unsubstituted or substituted aryl, unsubstituted or substituted aryl$(C_1-C_6)$alkyl, unsubstituted or substituted aryl$(C_2-C_6)$alkenyl, halo, carboxy, $(C_1-C_6)$alkoxycarbonyl or $-(CH_2)_m-OH$, wherein m is 1, 2 or 3;

- - - indicates a single or a double bond;

X and Y are each independently hydrogen, or X and Y together represent a bridge of the formula $-(CH_2)n-$, where n is 1 or 2;

$A_1$ and $A_2$ are each independently an unsubstituted or substituted aryl;

Z is $-CO-$, $-SO_2-$ or $-CH_2-$;

provided that, when Z is $-CO-$, $A_1$ is not 3,4,5-trimethoxyphenyl;

or a pharmaceutically-acceptable salt or ester thereof.

3. A method of treating an animal, including a human, suffering from or susceptible to pain associated with migraine, which method comprises administering a compound of the formula

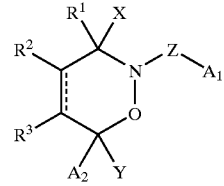

in which, $R^1$, $R^2$, and $R^3$ are independently hydrogen, $(C_1-C_6)$alkyl, $(C_2-C_6)$alkenyl, $(C_3-C_{10})$cycloalkyl, unsubstituted or substituted aryl, unsubstituted or substituted aryl $(C_1-C_6)$alkyl, unsubstituted or substituted aryl$(C_2-C_6)$alkenyl, halo, carboxy, $(C_1-C_6)$alkoxycarbonyl or $-(CH_2)_m-OH$, wherein m is 1, 2 or 3;

- - - indicates a single or a double bond;

X and Y are each independently hydrogen, or X and Y together represent a bridge of the formula $-(CH_2)n-$, where n is 1 or 2;

$A_1$ and $A_2$ are each independently an unsubstituted or substituted aryl;

Z is $-CO-$, $-SO_2-$ or $-CH_2-$;

provided that, when Z is $-CO-$, $A_1$ is not 3,4,5-trimethoxyphenyl;

or a pharmaceutically-acceptable salt or ester thereof.

4. A method of treating an animal, including a human, suffering from or susceptible to a condition indicating the administration of a selective mnGluR1 antagonist which method comprises administering a compound of the formula

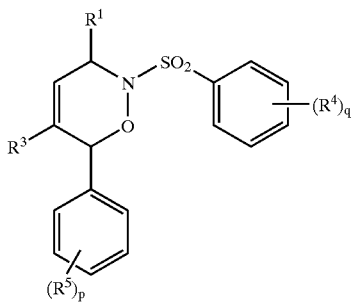

wherein,

R¹ and R³ are each independently hydrogen, or ($C_1$–$C_6$) alkyl;

R⁴ is amino, ($C_1$–$C_6$)acylamino, or a —NHCOO—($C_1$–$C_6$)alkyl;

R⁵ is ($C_1$–$C_6$)alkoxy; and p and q are each independently 1 or 2, or a pharmaceutically-acceptable salt or ester thereof.

5. A method of treating an animal, including a human, suffering from or susceptible to migraine, which method comprises administering a compound of the formula

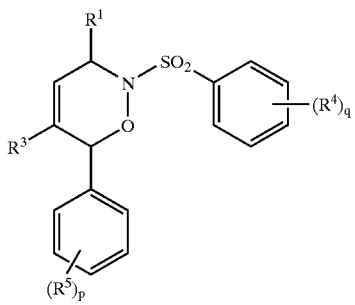

wherein,

R¹ and R³ are each independently hydrogen, or ($C_1$–$C_6$) alkyl;

R⁴ is amino, ($C_1$–$C_6$)acylamino, or a —NHCOO—($C_1$–$C_6$)alkyl;

R⁵ is ($C_1$–$C_6$)alkoxy; and p and q are each independently 1 or 2, or a pharmaceutically-acceptable salt or ester thereof.

6. A method of treating an animal, including a human, suffering from or susceptible to pain associated with migraine, which method comprises administering a compound of the formula

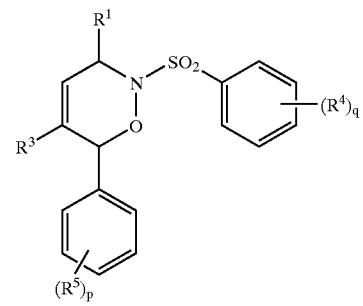

wherein,

R¹ and R³ are each independently hydrogen, or ($C_1$–$C_6$) alkyl;

R⁴ is amino, ($C_1$–$C_6$)acylamino, or a —NHCOO—($C_1$–$C_6$)alkyl;

R⁵ is ($C_1$–$C_6$)alkoxy; and p and q are each independently 1 or 2, or a pharmaceutically-acceptable salt or ester thereof.

7. A method of treating an animal, including a human, suffering from or susceptible to a condition indicating the administration of a selective mnGluR1 antagonist which method comprises administering a compound selected from the group consisting of 2-(4-Acetamidobenzenesulphonyl)-3,6-dihydro-3,5-dimethyl-6-(4-methoxyphenyl)-2H-1,2-oxazine, 2-(4-Acetamidobenzenesulphonyl)-3,6-dihydro-3,5-dimethyl-6-(4-ethoxyphenyl)-2H-1,2-oxazine, and 3,6-dihydro-3,5-dimethyl-6-(4-ethoxyphenyl)-2-(4-methylcarbamoylbenzenesulphonyl)-2H-1,2-oxazine, or a pharmaceutically-acceptable salt or ester thereof.

8. A method of treating an animal, including a human, suffering from or susceptible to migraine which method comprises administering a compound selected from the group consisting of 2-(4-Acetamidobenzenesulphonyl)-3,6-dihydro-3,5-dimethyl-6-(4-methoxyphenyl)-2H-1,2-oxazine, 2-(4-Acetamidobenzenesulphonyl)-3,6-dihydro-3,5-dimethyl-6-(4-ethoxyphenyl)-2H-1,2-oxazine, and 3,6-dihydro-3,5-dimethyl-6-(4-ethoxyphenyl)-2-(4-methylcarbamoylbenzenesulphonyl)-2H-1,2-oxazine, or a pharmaceutically-acceptable salt or ester thereof.

9. A method of treating an animal, including a human, suffering from or susceptible to pain associated with migraine which method comprises administering a compound selected from the group consisting of 2-(4-Acetamidobenzenesulphonyl)-3,6-dihydro-3,5-dimethyl-6-(4-methoxyphenyl)-2H-1,2-oxazine, 2-(4-Acetamidobenzenesulphonyl)-3,6-dihydro-3,5-dimethyl-6-(4-ethoxyphenyl)-2H-1,2-oxazine, and 3,6-dihydro-3,5-dimethyl-6-(4-ethoxyphenyl)-2-(4-methylcarbamoylbenzenesulphonyl)-2H-1,2-oxazine, or a pharmaceutically-acceptable salt or ester thereof.

\* \* \* \* \*

UNITED STATES PATENT AND TRADEMARK OFFICE
CERTIFICATE OF CORRECTION

PATENT NO.    : 6,482,824 B1  
DATED         : November 19, 2002  
INVENTOR(S)   : Clark et al.

It is certified that error appears in the above-identified patent and that said Letters Patent is hereby corrected as shown below:

Title page,
Item [22], PCT Filed date, please delete "Nov. 1, 2000" and insert -- Nov. 1, 1999. --

Column 17,
Line 59, please delete "$(C_{1-c6})$" and insert -- $(C_1-C_6)$ --.

Column 18,
Line 66, please delete "mnGluR1" and insert -- mGluR1 --.

Column 20,
Line 25, please delete "mnGluR1" and insert -- mGluR1 --.

Signed and Sealed this

Twenty-second Day of April, 2003

JAMES E. ROGAN
*Director of the United States Patent and Trademark Office*